United States Patent [19]

Karll et al.

[11] 4,384,138
[45] May 17, 1983

[54] PROCESS AND COMPOSITIONS

[75] Inventors: Robert E. Karll, Batavia; Richard J. Lee, Downers Grove, both of Ill.

[73] Assignee: Standard Oil Company (Indiana), Chicago, Ill.

[21] Appl. No.: 945,316

[22] Filed: Sep. 25, 1978

Related U.S. Application Data

[63] Continuation-in-part of Ser. No. 831,732, Sep. 9, 1977, Pat. No. 4,142,980.

[51] Int. Cl.³ ............................................. C07C 65/01
[52] U.S. Cl. ..................................... 562/478; 208/19; 252/56 R
[58] Field of Search ........................................ 562/478
[56] References Cited

U.S. PATENT DOCUMENTS 3,721,704 3/1973 Dexter .................................. 562/478
4,142,980 3/1979 Karll .................................. 252/51.5 A

OTHER PUBLICATIONS

Wagner & Zook, Synth. Org. Chem (1965), pp. 232, 233, 480.

Primary Examiner—Alan Siegel
Attorney, Agent, or Firm—Richard A. Kretchmer; William T. McClain; William H. Magidson

[57] ABSTRACT

Disclosed are substituted phenol comprising the reaction product of an alkyl phenol, said alkyl substituent containing about 50 to about 20,000 carbon atoms, and aliphatic unsaturated carboxylic acid containing about 3 to about 100 carbon atoms; and a process for the manufacture of said substituted phenol. The substituted phenol can have the formula

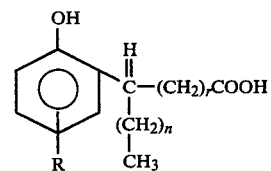

where R comprises alkyl substituent containing from about 50 to about 20,000 carbon atoms, and n and r are integers such that $n+r \geq 5 \leq 15$.

2 Claims, No Drawings

PROCESS AND COMPOSITIONS

RELATED APPLICATIONS

This application is a continuation-in-part of U.S. Ser. No. 831,732, filed Sept. 9, 1977 now U.S. Pat. No. 4,142,980.

BACKGROUND

This invention relates to certain compounds and processes for their manufacture. More specifically, it relates to compositions and processes useful in the manufacture of lubricating oil additives, especially dispersants and detergents.

Present-day automobile and diesel engines have been designed for higher power output, lower combustion products emission and longer in-service periods of use of crankcase lubricating oils. These design changes have resulted in such severe operating conditions as to necessitate devising higher efficiency lubricating oils that will, under the increased severity of in-service use, afford proper protection against corrosion and the accumulation or deposition of sludge, varnish and resinous materials on the surface of engine parts which rapidly accelerate decrease in both operating efficiency and life of the engine. The principal ingredient of crankcase lubricants is a base lubricating oil, a mixture of hydrocarbons usually derived from petroleum. Even when highly refined by removal of deleterious components, such as polymerizable components, acid formers, waxes, etc., a lubricant base oil still requires the addition of a number of oil-soluble chemical additives to enable the oil to resist oxidation, deposition of sludge and varnish on, and corrosion of, the lubricated metal parts, and to provide added lubricity and regulated viscosity change from low to high temperature. These ingredients are commonly known as anti-oxidants, dispersant-detergents, pour point dispersants, etc.

Combustion products from the burning of fuel and thermal degradation of lubricating oils and addition agents tend to concentrate in the crankcase oil with the attendant formation of oil-insoluble deposit-forming products, that either surface coat the engine parts with varnish or lacquer-like films or settle out on the engine parts as viscous sludge deposits or form solid ash-like or carbonaceous deposits. Any of such deposits can restrict, and even plug, grooves, channels and holes provided for lubricant flow to the moving surfaces of the engine requiring lubrication, thus accelerating the wear and reducing the efficiency of the engine. In addition, acidic combustion products corrode the lubricated metal surfaces. Chemical additives are blended in crankcase oil formulations not only to reduce thermal decomposition of the oil and addition agents (anti-oxidants) but also to keep in suspension (as a dispersant) and to resuspend (as a detergent) insoluble combustion and degradation products as well as to neutralize acidic products (anti-corrosion agents). A separate additive is commonly added for each improvement to be effected.

Numerous detergents or dispersants for lubricating oils have been developed, some of which are based on a substituted phenol as an intermediate. For example, substituted phenols can be reacted with formaldehyde and an amine having a reactive nitrogen in a Mannich condensation reaction, thereby affording an oil soluble lubricating oil additive. Commonly used substituted phenols are alkyl substituted, especially polymer substituted phenols.

Polymer-substituted phenols having the formula:

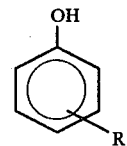

are well known in the art. Typically, R is derived from polypropylene or polybutene having an average number of carbon atoms ranging from about 50 to about 20,000. The polymer-substituted phenol can be prepared by alkylating phenol with the polymer in the presence of $BF_3$ catalyst. This procedure and products formed thereby are disclosed in British Pat. No. 1,159,368. $BF_3$ is generally the catalyst of choice for the alkylation reaction. Other Friedel-Crafts catalysts such as $AlCl_3$ are generally unsatisfactory because their use results in extensive degradation of the polymer. Even with the use of $BF_3$ the alkylation must be carried out under carefully controlled reaction conditions to minimize polymer degradation. Because of the susceptibility to degradation of the polymer substituent, attempts to further alkylate polymer-substituted phenols under Friedel-Crafts conditions have generally been unsuccessful. It is often desirable to further substitute the alkyl phenol to improve oil solubility and possibly improve the effectiveness of reaction products made therefrom.

It is an object of this invention to provide a process for the alkylation of alkyl phenol which does not substantially degrade the alkyl group.

It is an object of this invention to provide a multi-substituted phenol which is useful in the manufacture of lubricating oil additives.

It is further an object of this invention to provide intermediates for the manufacture of highly effective lubricating oil detergents or dispersants.

SUMMARY OF THE INVENTION

Disclosed are substituted phenol compositions and a process for the manufacture of said substituted phenols. These phenols are useful in the manufacture of Mannich condensation products. The Mannich products can be used in small amounts to improve the detergent or dispersancy properties of lubricating oils.

Generally, the substituted phenol comprises reaction product of alkyl phenol and aliphatic unsaturated carboxylic acid. The alkyl phenol can be mono or dialkyl substituted, but mono substitution in the para position is preferred. The alkyl group commonly contains from about 50 to about 20,000 carbon atoms, but more preferably contains about 200 to about 300 carbon atoms. The alkyl phenol is commonly formed by alkylation of phenol with a monoolefin, especially polymeric olefins made by the polymerization of $C_2$–$C_6$ olefins. The most commonly used polymeric olefins are polybutene and polypropylene, especially polybutene. Alkylation of phenol with a monoolefin using boron trifluoride catalyst, at reaction temperatures of below about 65° C., preferably in the range of 40°–50° C., is the preferred process for the preparation of suitable alkylphenols.

The alkyl phenol is reacted with an aliphatic unsaturated carboxylic acid generally containing about 3 to about 100 carbon atoms. Preferably, the unsaturated acid contains about 6 to about 40, more preferably from about 8 to about 18 carbon atoms. The aliphatic unsaturated carboxylic acid may contain a double bond in any position, such as α, β or otherwise unsaturated. In some cases the acid may contain more than one double bond, or additional functionality or substitution, so long as it does not interfere with the solubility of the product substituted phenol, Mannich reaction product thereof, or interfere with the Mannich reaction. Some examples of suitable acids are oleic, undecylenic, acrylic, isocrotonic, methacrylic, sorbic, maleic, and others. Oleic acid is a preferred acid. It is preferred that the unsaturated acid be in this CIS configuration in that the alkylation reaction takes place more readily. Aliphatic unsaturated carboxylic acids are commercially available, or can be made, for example, by oxidation of aliphatic hydrocarbons or can be found in beef tallow, coconut oil, corn oil, cottonseed oil, lard oil, palm oil, olive oil, peanut oil, soybean oil, and the like.

The alkylation of alkyl phenol with aliphatic unsaturated carboxylic acid can be conducted in the presence of a catalytically effective amount of $BF_3$ and HCOOH. Although effective catalysis can be conducted over a range of $BF_3$:HCOOH ratios, good selectivity can be achieved using a catalyst comprising a molar ratio of about 2 HCOOH for every mole of $BF_3$. The catalyst can be prepared by bubbling $BF_3$ into formic acid cooled to about 0° C. until absorption of $BF_3$ ceases. At this point, increase in weight indicates that about 1 mole of $BF_3$ has been absorbed for 2 moles of formic acid. The alkylation of alkylphenol with aliphatic unsaturated carboxylic acid is commonly conducted at a temperature from about 50° F. to about 250° F., preferably from about 80° F. to about 250° F., still more preferably, in the range from about 150° F. to about 200° F. The alkylation reaction can be conveniently carried out in an inert solvent. Hydrocarbon solvents such as hexane, heptane, octane and the like are inexpensive, readily available and particularly useful. In the general alkylation procedure, about one equivalent weight of polymer-substituted phenol is dissolved in an equal weight of solvent such as hexane together with up to about one equivalent weight of $BF_3.2$ HCOOH catalyst. Under vigorous agitation, one equivalent of the aliphatic unsaturated acid is added slowly. When all of the acid has been added agitation is continued until the reaction is essentially completed. Typically the reaction is completed within about 24 hours, generally in about 3–4 hours. Upon settling, the catalyst layer is drawn off and the hexane layer is washed with methanol and then water. The hexane layer can then be distilled to remove hexane and water and to yield the desired substituted phenol. While the substituted phenol contains a mixture of alkylated products, most commonly the desired product is a disubstituted phenol containing one alkyl group and one group from the unsaturated acid.

The method of alkylating an alkyl-substituted phenol having the formula:

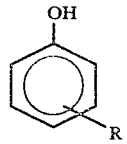

where R comprises alkyl substituent containing from about 50 to about 20,000 carbon atoms, with aliphatic unsaturated carboxylic acid having from about 3 to about 100 carbon atoms with no substantial degradation of said R substituent generally comprises reacting 1 equivalent of said alkyl substituted phenol with about 1 equivalent weight of said aliphatic unsaturated acid in the presence of a catalytically active amount of $BF_3$ and HCOOH.

This process can be used to manufacture disubstituted phenol having the formula:

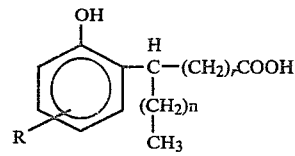

where R comprises alkyl substituent containing from about 50 to about 20,000 carbon atoms, and n and r are integers such that $n+r \leq 5 \geq 15$.

The previously described substituted phenols are extremely useful for reaction with an amine having at least one reactive nitrogen and a formaldehyde affording reactant in a Mannich condensation. This oil soluble condensation product is a highly effective detergent or dispersant in lubricating oils. Commonly, the oil soluble Mannich reaction product comprises the reaction product of (a) the reaction product of an alkyl phenol, said alkyl substituent containing about 50 to about 20,000 carbon atoms, and an aliphatic unsaturated carboxylic acid containing about 3 to about 100 carbon atoms; (b) an amine having at least one reactive nitrogen and containing less than about 100 carbon atoms; and (c) a formaldehyde affording reactant. The molar ratio of a:b:c is about 1:0.7-1.0:1.5-2, preferably about 1:1:1.5.

The formaldehyde affording reactant may be free formaldehyde, aqueous solution of formaldehyde or a polymerized form of formaldehyde which can provide monomeric formaldehyde under the reaction conditions. Aqueous formaldehyde is conveniently used.

The amine can be any one of a wide range of amines having a reactive nitrogen group, and generally contains less than about 100 carbon atoms. One group of particularly useful amines is polyamines such as those having the general formula:

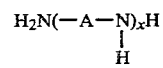

wherein A is a divalent alkylene radical of 2 to 6 carbon atoms and x is an integer of 1 to 10. More commonly, A is a divalent alkylene radical of 2 to 3 carbon atoms and x is an integer of 2 to 6. Commonly used polyamines are ethylene- and propylene-polyamines and including ethylenediamine, diethylenetriamine, triethylenetetramine, tetraethylenepentamine, pentaethylenehexamine, hexaethyleneheptamine, propylenediamine, dipropylenetriamine, tripropylenetetramine, tetrapropylenepentamine, pentapropylenehexamine, and hexapropyleneheptamine. The ethylenepolyamines are preferred, especially tetraethylenepentamine. These polyamines can be prepared by well-known methods of the art such as by the reaction of ethylene or propylenedichloride with ammonia. Most of the above polyamines are commercially available.

When a polyamine which has more than two amino groups is a reactant, and more than two moles each of alkylphenol and formaldehyde per mole of polyamine are used, the internal amino groups may also have alkyl- and hydroxy-substituted benzyl substituents. Depending upon the particular polyamine used, the particular ratio of alkylphenol and formaldehyde to polyamine employed, the reaction product may have none, some, or all of the internal amino groups of the polyamine substituted with an alkyl- and hydroxy-substituted benzyl group.

Any amine used may have additional substitutions so long as it does not destroy the oil solubility of the final Mannich compound, and does not interfere with the Mannich condensation. For example, hydroxyl substituted amines can commonly be used.

The Mannich reaction product is commonly prepared by mixing together substituted phenol, amine and formaldehyde affording reactant and heating them to a temperature sufficient for the reaction to occur, which is in the range of about 100° F. to about 350° F., preferably in the range of about 200° F. to about 350° F. The reaction mixture is commonly kept at the reaction temperature until sufficient water of condensation has been evolved and removed. The reaction may be carried out in the absence of a solvent, but it is preferable to use a solvent, preferably one which distills with water azeotropically. Suitable solvents include hydrocarbons boiling in the range of 50° C. to 200° C. and include, among others, hexane, cyclohexane, benzene, toluene, and xylene. The amount of solvent is not critical, but when it is used it may be present in an amount of from about 1–75% by weight of the total reaction mixture.

The lubricating oils in which the compositions of this invention are useful as additives and which comprise a major proportion of the lubricating oil compositions may be of synthetic, animal, vegetable, or mineral origin. Ordinarily mineral lubricating oils are preferred by reason of their availability, general excellence, and low cost. For certain applications, oils belonging to one of the other three groups may be preferred. Normally the lubricating oils preferred will be fluid oils ranging in viscosity from about 40 Saybolt Universal seconds at 100° F. to about 200 Saybolt Universal seconds at 210° F. This invention contemplates also the presence of other additives in lubricating compositions. Such additives include, for example, viscosity index improving agents, pour point depressant agents, anti-foam agents, extreme pressure agents, rust-inhibiting agents, and oxidation and corrosion inhibiting agents.

The Mannich additive of this invention is generally added to lubricating oil in order to improve the detergency or dispersancy properties of said oil. Depending on the nature of the oil, the intended use and the desired improvement, different amounts of the additive are needed in order to be effective. Generally about 0.05 to about 5 weight percent, preferably from about 0.1 to about 2 weight percent, of the additive is used.

The invention may be more readily understood by reference to the following examples.

EXAMPLE 1

For the preparation of high molecular weight disubstituted phenol, 870 g of polybutylene phenol, equivalent to 0.25 mole was diluted with 500 ml of hexane. The molecular weight of the polybutyl substituent was about 3500 and contained an average number of carbon atoms of about 240. To the solution was added 80 g of $BF_3 \cdot HCOOH$ catalyst, equivalent to 0.5 mole. Under vigorous agitation, 72 g of oleic acid, equivalent to 0.25 moles, was introduced dropwise over a period of about ½ hour. A slight exothermic reaction occurred, raising the reaction temperature by six degrees. The reaction was held at room temperature for 24 hours after which the catalyst layer was removed. The oil layer was washed with methanol and then water. The hexane solution was then distilled to a pot temperature of 250° F. to remove all solvent and water. The residual disubstituted phenol reaction product was obtained as a clear distillation residue. The product consists essentially of 8-(1-hydroxy-4-polybutyl)phenol stearic acid in mineral oil.

EXAMPLE 2

To the entire amount of the disubstituted phenol prepared in Example 1 was added 48 g (0.25 mole) of tetraethylenepentamine. The reaction mixture was heated to 350° F. and held at this temperature for 2 hours. The reaction mixture was cooled to 150° F. and 40.5 g of 36% aqueous formaldehyde was added dropwise thereto. The mixture was then slowly heated to 300° F. with nitrogen sparging to remove water. The reaction mixture was then diluted with SAE 5W oil and filtered over Celite clay. The filtrate comprised a solution containing 30% of Mannich condensation product in SAE 5W oil. The nitrogen content of the solution was 1.41%.

EXAMPLE 3

A solvent-extracted mineral oil solution of 0.66 mole of 1600 molecular weight monosubstituted polybutyl phenol was reacted with 0.61 mole of tetraethylenepentamine, 1.2 moles formaldehyde and 0.33 mole of oleic acid and the reaction mixture heated to 300° F. for three hours with nitrogen gas purging to remove water. The Mannich reaction product was then filtered through diatomaceous earth to yield a crystal clear filtrate of 1.4% nitrogen content and a SSU viscosity at 210° F. of 1070. The function of the oleic acid was to prevent haze formation during processing and in storage. No substantial amount of this acid, if any, becomes attached to the phenol.

The use of the Mannich product of Example 2 as a dispersant addition agent in lubricating oils is demonstrated in the Spot Dispersancy Test and in the Ford Sequence V-C Test. In the Spot Dispersancy Test, a measured amount of the Mannich product is thoroughly mixed with a measured amount of used test oil (crankcase oil resulting from a Lincoln Engine Sequence V Test run for 384 hours), and the stirred mixture is heated to 360° F. for 16 hours. The used crankcase oil from the Lincoln Test contains sludge to the extent that the original dispersant was no longer capable of keeping the sludge suspended in the oil. As a control for purposes of comparison, the same volume of used crankcase oil is likewise heated and stirred at 360° F. for 16 hours without the addition of any further dispersant. Equal aliquot portions of each of the test oils are deposited on different marked areas of a large sheet of blotter paper. The blotter paper is held at room temperture for 3 hour development (low severity) and for 27 hour development (high severity). The spots develop into two separate concentric rings: the inner ring is the sludge ring and the outer ring is the sludge-free oil ring. The diameters of these rings are measured and the ratio of the diameter of the sludge ring ($D_s$) to the diameter of the oil ring ($D_o$) times 100 provides an indication of the dispersancy function of the test compound. Ideally the ratio should be 100.

TABLE I

| | | Spot Dispersancy Test $D_s/D_o \times 100$ | |
|---|---|---|---|
| Dispersant | Conc. | Low Severity (3 hr development) | High Severity (27 hr development) |
| Example 2 | 3% | 100% | 89.5% |
| Example 2 | 1.5% | 90% | 79.5% |
| Example 3 | 4.0% | 90% | 72% |
| Control | — | 55% | 45% |

The Ford Sequence V-C Test is specified in *ASTM STP 315F,* Multicylinder Test Sequences for Evaluating Automotive Oils. Briefly, sequence V-C describes an engine testing procedure that evaluates crankcase motor oil with respect to sludge and varnish deposits produced by engine operation under a combination of low and mid range temperatures. The test uses a 302 C.I.D., V-8, "Sequence V-C Oil Test Engine and Parts Kit" obtained from Ford Motor Company. The test engine is completely disassembled, cleaned, and rebuilt in a specified manner. It is then installed on a dynamometer test stand equipped with appropriate accessories for controlling speed, load, and other conditions. It is operated with certified MS-08 fuel in three stages. During Stage I, the engine is operated for 120 minutes at high power output with moderate oil and water temperatures and a lean air/fuel ratio (A/F). Stage II operates for an additional 75 minutes at higher oil and water temperatures. During Stage III, the engine is operated for 45 minutes at low rpm, with low oil and water temperatures, and with a rich A/F. Four cycles each of four hours duration are run each day until 48 cycles (192 engine operating hours) are accumulated. At the conclusion of the test, the engine is completely disassembled to determine the extent of wear, sludge, varnish, and valve deposits.

With 5% of the product of Example 2 in a conventional crankcase oil blend, the following results were obtained in the Ford Sequence V-C Test:

| Sludge (10 = perfect) | Varnish (10 = perfect) |
|---|---|
| Ave. of 10 engine parts = 9.7 | Ave. of 10 engine parts = 8.6 |
| Required for passing = 8.5 | Required for passing = 8.3 |
| | Piston Skirt = 8.6 |
| | Required for passing = 8.2 |

From the data shown above, it is clear that the compositions of this invention provide superior dispersancy properties in lubricating oils.

We claim:

1. A disubstituted phenol having the formula:

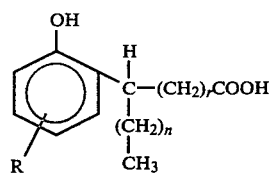

where R comprises alkyl substituent containing from about 50 to about 20,000 carbon atoms, and n and r are integers such that $n + r \leqq 5 \geqq 15$.

2. The disubstituted phenol of claim 1 wherein R contains from about 200 to about 300 carbon atoms.

* * * * *

UNITED STATES PATENT OFFICE
CERTIFICATE OF CORRECTION

Patent No. 4,384,138            Dated May 17, 1983

Inventor(s) Robert E. Karll and Richard J. Lee

It is certified that error appears in the above-identified patent and that said Letters Patent are hereby corrected as shown below:

Column 4, line 19, "$n + r \leq 5 \geq 15$" should read
--$n + r \geq 5 \leq 15$--.

Column 8, line 33, "$n + r \leq 5 \geq 15$" should read
--$n + r \geq 5 \leq 15$--.

Signed and Sealed this

Fourteenth Day of February 1984

[SEAL]

Attest:

GERALD J. MOSSINGHOFF

Attesting Officer      Commissioner of Patents and Trademarks